United States Patent [19]

Roe et al.

[11] 4,093,725

[45] June 6, 1978

[54] (3-ALKYLAMINO-2-HYDROXYPROPOXY)-1-HYDRAZINOPHTHALAZINES

[75] Inventors: Anthony Maitland Roe, Hatfield; Robert Anthony Slater, Letchworth; Edwin Michael Taylor, Welwyn, all of England

[73] Assignee: Smith Kline & French Laboratories Limited, Welwyn Garden City, England

[21] Appl. No.: 763,946

[22] Filed: Jan. 31, 1977

[30] Foreign Application Priority Data

Feb. 9, 1976 United Kingdom .............. 04896/76

[51] Int. Cl.$^2$ ..................... A61K 31/50; C07D 237/34
[52] U.S. Cl. ...................................... 424/250; 544/237
[58] Field of Search ..................... 260/250 P; 424/250

[56] References Cited

U.S. PATENT DOCUMENTS 4,011,321  3/1977  Coates ................................. 424/250

*Primary Examiner*—Paul M. Coughlan, Jr.
*Attorney, Agent, or Firm*—Joan S. Keps; Richard D. Foggio; William H. Edgerton

[57] ABSTRACT

The compounds are substituted hydrazinophthalazines which are active as β-adrenergic blocking agents and as vasodilators. A specific compound of the invention is 5-(3-t-butylamino-2-hydroxypropoxy)-1-hydrazinophthalazine.

12 Claims, No Drawings

(3-ALKYLAMINO-2-HYDROXYPROPOXY)-1-HYDRAZINOPHTHALAZINES

This invention relates to pharmacologically active compounds and in particular to certain substituted hydrazinophthalazines which are active as β-adrenergic blocking agents and as vasodilators. It also relates to processes for the production of said compounds, to pharmaceutical compositions comprising them and to methods of treatment employing their use.

The compounds of the present invention may be represented by the following Formula 1:

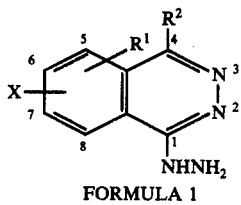

FORMULA 1 wherein $R^1$ is hydrogen, lower alkyl, halogen, lower alkoxy or di lower alkylamino; $R^2$ is hydrogen, methyl, halogen, benzyl or substituted benzyl; and X is a group of the formula

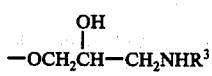

wherein $R^3$ is isopropyl, t-butyl or phenylethyl; or hydrates, pharmaceutically acceptable salts, and hydrated salts thereof.

Throughout the present specification, by the term, "lower alkyl" and "lower alkoxy" we mean alkyl and alkoxy groups containing a chain of no more than four carbon atoms, which chain may, where possible, be branched.

Preferably $R^1$ is hydrogen, chloro or methyl,
Preferably $R^2$ is hydrogen or methyl,
Preferably $R^3$ is isopropyl or t-butyl,
Preferably X is in the 5-position of the phthalazine ring.

It is further preferred that when $R^1$ is other than hydrogen and X is in the 5-position of the phthalazine ring, $R^1$ is in the 7 or 8 position.

A specific preferred compound of the invention is 5-(3-t-butylamino-2-hydroxypropoxy)-1-hydrazinophthalazine.

The compounds of Formula 1 may be prepared by a series of reactions illustrated in Scheme 1. The hydroxy group of the compounds of Formula 2 is first converted into the substituent X, where X is as defined in Formula 1. The compound of Formula 2 is treated with an epihalohydrin to give the compound of Formula 3, which on reaction with an amine of formula $R^3NH_2$ yields the compound of formula 4. Acetylation of this latter compound (Formula 4) and treatment of the product with phosphorus pentasulphide yields the compound of Formula 6 (often obtained in admixture with the compound of Formula 6a), and removal of the protecting acetyl (and/or thioacetyl) groups gives the compound of Formula 7 which by treatment with hydrazine, is converted into the required compound of Formula 1.

It will also be understood that an alternative series of reactions are possible, wherein the various reactive groupings present in the compounds of our invention may be introduced at different stages from those illustrated in the attached reaction scheme. For example, the hydrazino group may first be introduced into the 1-position of the compound of Formula 2. Protection of this group, for example by reacting it with a suitable reagent such as an alkoxycarbonyl halide, a ketone such as acetone or an aldehyde such as benzaldehyde may be followed by introduction of the 3-alkylamino-2-hydroxy-1-propoxy side chain. Finally, removal of the hydrazino protecting group (e.g. with acid) yields the required compound of Formula 1.

SCHEME 1

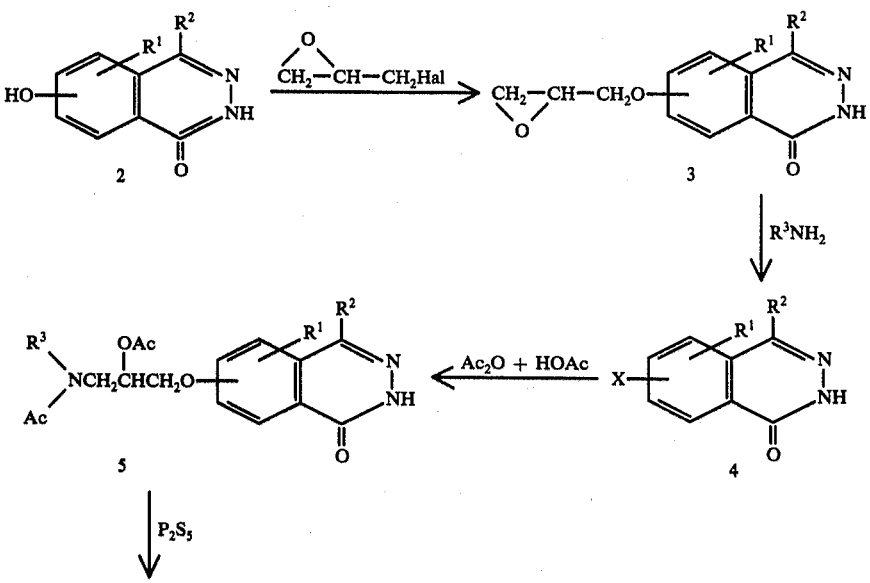

SCHEME 1 -continued

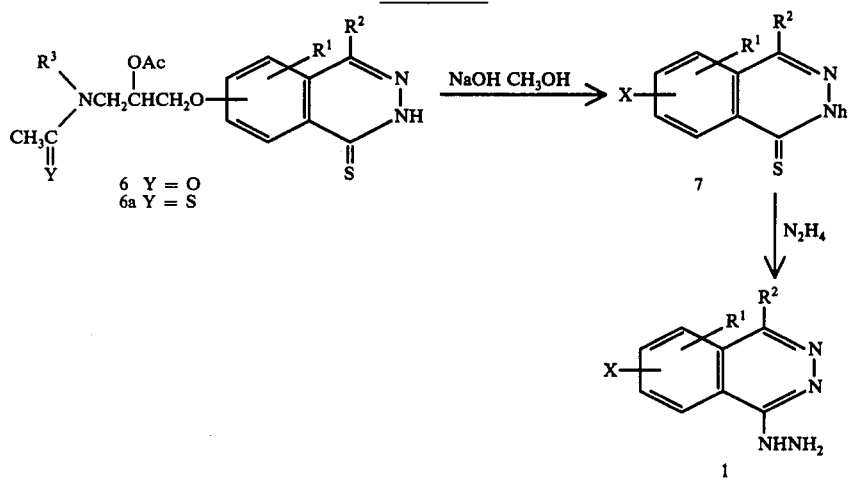

As stated above, the compounds of Formula 1 are β-adrenergic blocking agents and vasodilators. β-Adrenergic blocking agents are useful in the treatment of angina pectoris, cardiacarrhythmia and hypertension and vasodilators are often used in the treatment of hypertension. It will be appreciated that those compounds of the present invention which exhibit concomitant β-adrenergic blocking and vasodilator activity such as to cause a fall in blood pressure without tachycardia in man, are particularly useful.

The β-adrenergic blocking activity of our compounds may be demonstrated in a suitable test preparation such as cats anaesthetised with pentobarbitone sodium (Nembutal), 60mg/kg i.p. In such anaesthetised cats, intravenous injections of isoprenaline cause tachycardia and vasodilatation in the hind limb. These effects of isoprenaline, which are dose-dependent and are due to stimulation of β-adrenoreceptors can be reduced or abolished by intravenous administration of from 0.01 to 100 micromoles/kg of the β-adrenergic blocking agent of Formula 1.

Two tests may be used in the estimation of vasodilatation. In the first of these, the fall in blood pressure is measured in rats of a spontaneously hypertensive strain to which our compounds have been subcutaneously or orally administered in a concentration of from 0.1 to 1000 micromoles/kg. Over a period of 6 hours commencing one hour before the administration of the compound the blood pressure and heart rate are monitored directly from indwelling polythene cannulae placed in the carotid artery. In the second test vasodilatation is measured directly as a decrease in vascular resistance of the autoperfused hindquarters of anaesthetised rats injected intraarterially or intravenously with from 0.1 to 100 micromoles/kg of a compound of Formula 1.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric, acetic, citric and maleic acids.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 500 mg. If a liquid carrier is used, the preparation may be in the form of a syrup, emulsion, soft gelatin capsule, sterile injectable liquid such as in an ampoule or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to produce β-adrenergic blockade and vasodilatation. The route of administration may be oral or parenteral.

Preferably, each dosage unit will contain the active ingredient in an amount of from about 25 mg to about 500 mg, most preferably from about 50 mg to about 250 mg.

The active ingredient will probably be administered in equal doses one to three times per day. The daily dosage regimen will preferably be from about 100 mg to about 2 g.

Other pharmacologically active compounds may in certain cases be included in the composition. Advantageously the composition will be made up in a dosage unit form appropriate to the desired mode of administration, for example as a tablet, capsule or injectable solution.

The invention is illustrated but in no way limited by the following examples wherein all temperatures are given in degrees Centigrade:

EXAMPLE 1

5-(3-t-Butylamino-2-hydroxypropoxy)-1-hydrazinophthalazine (i) A stirred solution of 3-hydroxy-4-nitrophthalide (43.4 g, 0.22 mole) and hydrazine hydrate (11.6 ml) in ethanol (1830 ml) was heated under reflux for 1 hour. The heating was discontinued and palladium on carbon (10%, 2.44 g) was added (with caution) over 15 minutes. A solution of hydrazine hydrate (24.2 ml) in ethanol (304 ml) was then added, dropwise, over 30 minutes and the mixture was heated under reflux for a further 2.5 hours. Filtration of the hot reaction mixture followed by the addition of a saturated solution of hydrogen chloride in ethanol (80 ml) to the filtrate gave a solid precipitate which was collected and washed with ethanol and ether. Evaporation of the filtrate gave a solid residue which was washed several times with boiling ethanol. The combined solids were recrystallised from water, after charcoal treatment, to give 5-amino-1(2H)-phthalazinone (12.7 g, 35%, m.p. 289°–291°).

(Found: C, 59.48; H, 4.35; N, 26.18; $C_8H_7N_3O$ requires: C, 59.61; H, 4.37; N, 26.07%).

(ii) Concentrated sulphuric acid (8 ml) was added to a stirred mixture of 5-amino-1(2H)-phthalazinone (9.4 g, 0.058 mole) and water (50 ml). The resultant stirred paste was cooled in ice and diazotised by the addition of sodium nitrite (4.15 g, 0.06 mole) in water (15 ml). The filtered diazonium sulphate solution was added over 1.5 hours to a stirred boiling solution of concentrated sulphuric acid (30 ml) and boric acid (5.42 g, 0.088 mole) in water (200 ml). The solution was heated for a further 30 minutes then cooled and the collected solid was washed with water to give 5-hydroxy-1(2H)-phthalazinone 9.12 g, 96% m.p. 351°–355°). 5-Hydroxy-1(2H)-phthalazinone was purified as the 5-acetoxy derivative m.p. 162° (ethanol).

(iii) A well stirred mixture of potassium carbonate (6.65 g, 0.048 mole), epibromohydrin (20.6 ml, 0.24 mole), dry butan-2-one (400 ml), and finely ground 5-hydroxy-1(2H)-phthalazinone (7.76 g, 0.048 mole) was heated under reflux for 27 hours. Evaporation of the filtered solution under reduced pressure gave an oil (9 g) which was purified on a silica column by elution with mixtures of chloroform and methanol and crystallisation of the concentrated eluate from 2-propanol to give 5-(2,3-epoxypropoxy)-1(2H)-phthalazinone (3.58 g, 34%, m.p. 173°–174°)

(Found: C, 60.46; H, 4.75; N, 12.98; $C_{11}H_{10}N_2O_3$ requires: C, 60.54; H, 4.62; N, 12.84%).

(iv) A stirred mixture of 5-(2,3-epoxypropoxy)-1(2H)-phthalazinone (3.74 g, 0.017 mole), methanol (80 ml), and t-butylamine (11 ml, 0.1 mole) was heated under reflux for 2 hours. Additional t-butylamine (5 ml, 0.047 mole) was added and the solution was heated under reflux for a further hour. Evaporation under reduced pressure gave a foam (4.89 g, 98%) which was purified on a silica column by elution with mixtures of chloroform and methanol to give 5-(3-t-butylamino-2-hydroxypropoxy)-1(2H)-phthalazinone (3.33 g, 67%) obtained as a glassy foam by evaporation under reduced pressure.

(v) A mixture of 5-(3-t-butylamino-2-hydroxypropoxy)-1(2H)-phthalazinone (4.36 g, 0.046 mole), acetic anhydride (90 ml), and pyridine (4 drops) was heated on a steam bath for 1 hour with occasional swirling. The solution was evaporated under reduced pressure, the residue was treated with aqueous ethanol and evaporated. A solution of the residue in dichloromethane was washed successively with dilute hydrochloric acid and water. Evaporation of the dried solution gave a gum which was purified on a silica column by eluting with mixtures of chloroform and methanol and evaporation of the eluate to give 5-(2-acetoxy-3-N-acetyl-t-butylaminopropoxy)-1(2H)-phthalazinone (2.9 g, 50%) as a glassy foam.

(Found: M+, 375 $C_{19}H_{25}N_3O_5$ requires: M, 375).

(vi) Phosphorus pentasulphide (3.03 g, 0.014 mole) was added to a stirred solution of 5-(2-acetoxy-3-N-acetyl-t-butylaminopropoxy)-1(2H)-phthalazinone (2.56 g, 0.007 mole) in dry pyridine (50 ml) and the stirred mixture was heated under reflux for 2 hours. Additional phosphorus pentasulphide (1.5 g, 0.007 mole) was added to the partly cooled mixture which was then refluxed for a further 1 hour. When cool the supernatant pyridine solution was decanted from a viscous oil and diluted with an equal volume of water. After evaporation under reduced pressure the residue was distributed between water and ethyl acetate. The organic extract was successively washed with dilute hydrochloric acid and with water, dried, and evaporated to a yellow foam (2.3 g, 86%). Purification on a silica column by elution with mixtures of chloroform and methanol gave 5-(2-acetoxy-3-N-acetyl-t-butylaminopropoxy)-1(2H)-phthalazinthione (1.88 g, 70%) m.p. 162°–166°. (ethyl acetate).

(Found: M+, 391. $C_{19}H_{25}N_3O_4S$ requires, M, 391)

(vii) Aqueous sodium hydroxide solution (2N, 10.2 ml) was added to a stirred mixture of 5-(2-acetoxy-3-N-acetyl-t-butylaminopropoxy)-1(2H)-phthalazinthione (1.88 g, 0.0048 mole) and methanol (40 ml) and the solution was heated under reflux for 30 minutes. Evaporation under reduced pressure gave a residue which was dissolved in a small volume of water, and 25% aqueous acetic acid was added to pH 7. Excess of potassium carbonate was added an the crude product was collected and washed with water to give 5-(3-t-butylamino-2-hydroxypropoxy)-1(2H)-phthalzinethione (1.46 g, 99%, m.p. 192°–194.5°). Recrystallisation from aqueous 2-methoxyethanol gave a pure sample (1.1 g, 75%, m.p. 195°–196.5°).

(Found: C, 58.52; H, 7.11; N, 13.72; S, 10.42; M+, 307. $C_{15}H_{21}N_3O_2S$ requires: 58.62; H, 6.89; N, 13.67; S, 10.43%; M.307).

(viii) A stirred mixture of 5-(3-t-butylamino-2-hydroxypropoxy)-1(2H)-phthalazinthione (0.5 g), ethanol (50 ml) and hydrazine hydrate (15 ml) was heated under reflux for 21 hours. Ethanol and excess of hydrazine were removed by evaporation under reduced pressure to give 5-(3-t-butylamino-2-hydroxypropoxy)-1-hydrazinophthalazine (0.5 g, 100%) which was treated with 1.0N sulphuric acid (3.26 ml). Evaporation under reduced pressure gave the crude salt which was crystallised from aqueous methanol to give 5-(3-t-butylamino-2-hydroxypropoxy)-1-hydrazinophthalazine sulphate hydrate (0.45 g, 65%, m.p. 274°–276°, decomposition).

(Found: C, 42.96; H, 6.58; N, 16.54; S, 7.29; M+, 305. $C_{15}H_{23}N_5O_2 \cdot H_2SO_4 \cdot H_2O$ requires: C, 42.74; H, 6.46; N, 16.62; S, 7.61%: M(base), 305).

EXAMPLE 2

7-(2-Hydroxy-3-isopropylaminopropoxy)-1-hydrazinophthalazine (i) A hot solution of potassium permanganate (570 g, 3.6 mole) in water (1520 ml) was added in portions to a vigorously stirred mixture of 2-methyl-4-methoxyacetophenone (152 g, 0.93 mole) and potassium carbonate (76 g, 0.55 mole) in water (5700 ml) at 100°. The colour was allowed to discharge between additions, and the mixture was heated for a further 30 minutes after completion of the addition. The cold filtered solution was re-heated to 90° and the pH adjusted to 8.0. Hydrazine hydrate (51 g, 1.04 mole) was added and the volume of the solution was reduced to 3000 ml by evaporation. The filtered solution was made strongly acidic with hydrochloric acid and the resultant precipitate collected and washed with water. The solid was digested several times with methanol to leave a residue of 4-carboxy-7-methoxy-1(2H)-phthalazinone (51 g, 25%, m.p. 239°–240° (decomposition). The carboxylic acid was heated in an oil bath at 260° until evolution of carbon dioxide ceased (about 5 minutes), then immediately cooled. Soxhlet extraction of the product with water gave 7-methoxy-1(2H)-phthalazinone (41.3 g, 25%) m.p. 228°–229°).

(ii) A mixture of 7-methoxy-1(2H)-phthalazinone (62.5 g, 0.36 mole) and pyridine hydrochloride (150 g) was heated in an oil bath at 220° for 1 hour. The cold mixture was digested with aqueous sodium hydroxide and the resultant solution was washed with ether then acidified (pH6) with dilute hydrochloric acid. 7-Hydroxy-1(2H)-phthalazinone (54.5 g, 95%), m.p. 332°–333° was collected and washed with water.

(Found: C, 58.49; H, 3.72; N, 17.11; M+, 162. $C_8H_6N_2O_2$ requires: C, 58.53; H, 3.68; N, 17.07% M, 162).

(iii) 7-Hydroxy-1(2H)-phthalazinone was reacted with epibromohydrin in a similar manner to that described in Example 1(iii) to give 7-(2,3-epoxypropoxy)-1(2H)-phthalazinone, which after recrystallisation from ethyl acetate had m.p. 164°–166°.

(Found: C, 60.27; H, 4.61; N, 12.79; M+, 218 $C_{11}H_{10}N_2O_3$ requires: C, 60.54; H, 4.62; N, 12.84% M, 218)

(iv) 7-(2,3-Epoxypropoxy)-1(2H)-phthalazinone was reacted with isopropylamine in a similar manner to that described in Example 1(iv) to give 7-(2-hydroxy-3-isopropylaminopropoxy)-1(2H)-phthalazinone, the hydrochloride of which had m.p. 232°–235°.

(Found: C, 53.07; H, 6.57; Cl, 10.93; N, 12.99; $C_{14}H_{19}N_3O_3.HCl.O.2H_2O$ requires: C, 52.98; H, 6.48; N, 13.24; Cl, 11.17%

(v) 7-(2-Hydroxy-3-isopropylaminopropoxy)-1(2H)-phthalazinone was reacted with acetic anhydride in a similar manner to that described in Example 1(v) to give 7-(2-acetoxy-3-N-acetylisopropylaminopropoxy)-1(2H)-phthalazinone m.p. 143°–147°.

(vi) 7-(2-Acetoxy-3-N-acetylisopropylaminopropoxy)-1(2H)-phthalazinone was reacted with phosphorus pentasulphide in a similar manner to that described in Example 1(vi) to give a mixture of 7-(2-acetoxy-3-N-thioacetylisopropylaminopropoxy)-1(2H)-phthalazinethione and 7-(2-acetoxy-3-N-acetylisopropylaminopropoxy)-1(2H)-phthalazinethione which were obtained as glassy foams after separation on a silica column by elution with mixtures of chloroform and methanol.

(Found: M+ 393. $C_{18}H_{23}N_3O_3S_2$ requires M, 393. and M+ 377. $C_{18}H_{23}N_3O_4S$ requires M, 377)

(vii) A mixture of the products from (vi) was treated with sodium hydroxide in a similar manner to that described in Example 1(vii) until hydrolysis was complete, to give 7-(2-hydroxy-3-isopropylaminopropoxy)-1(2H)-phthalazinethione. The hydrochloride had m.p. 269°–271° (decomposition).

(Found: C, 51.12; H, 5.93; Cl, 10.75; N, 12.67; S, 9.51; M+, 293. $C_{14}H_{19}N_3O_2S$. HCl requires: C, 50.98; H, 6.11; Cl, 10.75; N, 12.74; S, 9.72%; M(base)293).

(viii) 7-(2-Hydroxy-3-isopropylaminopropoxy)-1(2H)-phthalazinethione was reacted with hydrazine hydrate in a similar manner to that described in Example 1(viii) to give 7-(2-hydroxy-3-isopropylaminopropoxy)-1-hydrazinophthalazine which was isolated as its hydrochloride m.p. 249°–253° (decomposition).

(Found: C, 45.84; H, 6.35; Cl, 18.99; N, 18.95; M+, 291. $C_{14}H_{21}N_5O_2$. 2 HCl. 0.25 $H_2O$ requires C, 45.60; H, 6.42; Cl, 19.23; N, 18.99%; M (base) 291).

EXAMPLE 3

7-(3-t-Butylamino-2-hydroxypropoxy)-1-hydrazinophthalazine.

(i) 7-(2,3-Epoxypropoxy)-1(2H)-phthalazinone was reacted with t-butylamine in a similar manner to that described in Example 1(iv) to give 7-(3-t-butylamino-2-hydroxypropoxy)-1(2H)-phthalazinone, the hydrochloride of which was recrystallised from ethanol and had m.p. 263°–264° (decomp).

(Found: C, 55.21; H, 6.82; Cl, 10.60; N, 12.80; M+, 291. $C_{15}H_{21}N_3O_3$ HCl requires: C, 54.96; H, 6.76; Cl, 10.82; N.12.82%; M(base)291).

(ii) 7-(3-t-Butylamino-2-hydroxypropoxy)-1(2H)-phthalazinone was reacted with acetic anhydride in a similar manner to that described in Example 1(v) to give 7-(2-acetoxy-3-N-acetyl-t-butylaminopropoxy)-1(2H)-phthalazinone m.p. 149°–152° (aqueous ethanol)

(Found: C, 60.58; H, 6.85; N, 11.03; $C_{19}H_{25}N_3O_5$ requires: C, 60.78; H, 6.71; N, 11.19%).

(iii) 7-(2-Acetoxy-3-N-acetyl-t-butylaminopropoxy)-1(2H)phthalazinone was reacted with phosphorus pentasulphide in a similar manner to that described in Example 1(vi) to give 7-(2-acetoxy-3-N-acetyl-t-butylaminopropoxy)-1(2H)-phthalazinthione which was recrystallised from ethanol-hexane and had m.p. 129°–131° (decomposition).

(Found: C, 58.08; H, 6.64; N, 10.46; S, 8.25; M+, 391; $C_{19}H_{25}N_3O_4S$ requires C, 58.29; H, 6.44; N, 10.73; S, 8.19% M, 391).

(iv) 7-(2-Acetoxy-3-N-acetyl-t-butylaminopropoxy)-1(2H)-phthazinthione was hydrolysed in a similar manner to that described in Example 1(vii) to give 7-(3-t-butylamino-2-hydroxypropoxy)-1(2H)-phthalazinthione, the hydrochloride of which was recrystallised from water and had m.p. 253°–256° (decomposition).

(Found: C, 60.65; H, 6.46; Cl, 10.30; N, 11.77; S, 9.01; M+, 307. $C_{15}H_{21}N_3O_2S$. HCl. 0.75$H_2O$ requires C, 50.41; H, 6.63; Cl, 9.92; N, 11.76; S, 8.97%; M(base)307).

(v) 7-(3-t-Butylamino-2-hydroxypropoxy)-1(2H)-phthalazinthione was reacted with hydrazine hydrate in a similar manner to that described in Example 1(viii) to give 7-(3-t-butylamino-2-hydroxypropoxy)-1-hydrazinophthalazine.

EXAMPLE 4

6-Bromo-7-(2-hydroxy-3-isopropylaminopropoxy)-1-hydrazinophthalazine (i) Bromine (20 g, 0.25 mole) was added to a stirred solution of 7-hydroxy-1(2H)phthalazinone (10g, 0.062 mole) in aqueous sodium hydroxide (2N, 140 ml), and the stirring was continued for two hours. An excess of sodium metabisulphite was added to the reaction mixture, and the precipitate was filtered off, washed with water and dried. This solid was suspended in acetic anhydride (17 ml) and was heated on a steam-bath for 30 minutes, and the solution was treated with charcoal, filtered and allowed to cool. The cooled mixture was filtered to give 7-acetoxy-6-bromophthalazone, which had m.p. 200°–201° after recrystallisation from ethanol. 7-Acetoxy-6-bromophthalazone was heated with 5% aqueous sodium hydroxide until a clear solution was obtained. The cooled solution was neutralised and the precipitate was filtered off to give 6-bromo-7-hydroxy-1(2H)-phthalazinone, m.p. > 320° (decomp.).

(ii) By subjecting 6-bromo-7-hydroxy-1(2H)-phthalazinone to a series of reactions similar to those described in Example 1(iii) and Example 2(iv–viii), 6-bromo-7-(2-hydroxy-3-isopropylaminopropoxy)-1-hydrazinophthalazine may be produced.

EXAMPLE 5

7-(3-t-Butylamino-2-hydroxypropoxy)-6-chloro-1-hydrazinophthalazine

Sodium hypochlorite solution (10% w/v chlorine, 175 ml) was added to a stirred solution of 7-hydroxy-1(2H)-phthalazinone (10 g, 0.062 mol) in aqueous sodium hydroxide (2N, 140 ml), and the stirring was continued for two hours. An excess of sodium metabisulphite was added to the reaction mixture, and the precipitate was recrystallised from ethanol to give 6-chloro-7-hydroxy-1(2H)-phthalazinone, m.p. > 340° (decomp), which was purified via the acetyl derivative m.p. 190°–192° as described in Example 4(i).

(ii) Substitution of 6-chloro-7-hydroxy-1(2H)-phthalazinone for 5-hydroxy-1(2H)-phthalazinone in the general procedure of Example 1(iii–viii) leads to the production of 7-(3-t-butylamino-2-hydroxypropoxy)-6-chloro-1-hydrazinophthalazine.

EXAMPLE 6

7-(3-t-Butylamino-2-hydroxypropoxy)-1-hydrazino-6-methylphthalazine (i) Treatment of 4-methyl-5-nitrophthalic acid with hot ammonium acetate in aqueous acetic acid and treatment of the product with 5% aqueous sodium carbonate gives 4-methyl-5-nitrophthalimide (ii) Treatment of 4-methyl-5-nitrophthalimide with sodium borohydride in 90% aqueous methanol and purification of the mixture gives 3-hydroxy-5-methyl-6-nitrophthalide.

(iii) Substitution of 3-hydroxy-5-methyl-6-nitrophthalide for 3-hydroxy-4-nitrophthalide in the general procedure of Example 1 gives the sulphate of the title compound.

EXAMPLE 7

5-(3-t-Butylamino-2-hydroxypropoxy)-1-hydrazino-4-methylphthalazine

Substitution of 5-amino-4-methyl-1(2H)phthalazinone for 5-amino-1(2H)-phthalazinone in the general procedure of Example (ii–viii) gives the sulphate of the title compound.

EXAMPLE 8

4-Benzyl-5-(2-hydroxy-3-isopropylaminopropoxy)-1-hydrazinophthalazine (i) 3-Benzylidene-4-nitrophthalide may be prepared by heating 3-nitrophthalic anhydride with phenylacetic acid and sodium acetate, triturating the product with aqueous sodium carbonate solution, and washing the residue. (ii) Substitution of 3-benzylidene-4-nitrophthalide for 3-hydroxy-4-nitrophthalide in the general procedure of Example 1 gives the sulphate of the title compound.

(iii) Substitution of
(a) 4-chlorophenylacetic acid
(b) 4-methoxyphenylacetic acid for phenylacetic acid in the above procedure leads to the production of
(a) 4-(4-chlorobenzyl)-5-(2-hydroxy-3-isopropylaminopropoxy)-1-hydrazinophthalazine sulphate
(b) 4-(4-methoxybenzyl)-5-(2-hydroxy-3-isopropylaminopropoxy)-1-hydrazinophthalazine sulphate.

EXAMPLE 9

6-(3-t-Butylamino-2-hydroxypropoxy)-1-hydrazine-7-methoxyphthalazine

3-Bromo-5-hydroxy-6-methoxyphthalide may be prepared by treating 5-hydroxy-6-methoxyphthalide with N-bromosuccinimide in chloroform. Treatment of 3-bromo-5-hydroxy-6-methoxyphthalide with hydrazine hydrate in boiling aqueous acetic acid gives 6-hydroxy-7-methoxy-1(2H)-phthalazinone, which may be converted into the sulphate of the title compound by the general procedure of Example 1.

EXAMPLE 10

5-(3-t-Butylamino-2-hydroxypropoxy)-4-chloro-1-hydrazinophthalazine (1) Treatment of 3-methoxyphthalic anhydride with hydrazine in boiling aqueous acetic acid gives 5-methoxyphthalhydrazide, which is converted into 1,4-dichloro-5-methoxyphthalazine by treatment with phosphorus pentachloride.

(2) Dimethylation of 1,4-dichloro-4-methoxyphthalazine with pyridine hydrochloride, and successive treatment of the product with epibromohydrin and potassium carbonate, t-butylamine, followed by treatment with hydrazine leads to the production of the title compound.

EXAMPLE 11

7-(3-t-Butylamino-2-hydroxypropoxy)-6-dimethylamino-1-hydrazinophthalazine (1) 7-Hydroxy-6-nitro-1(2H)-phthalazinone (which may be prepared by the nitration of 7-hydroxy-1(2H)-phthalazinone) is dissolved in aqueous sodium hydroxide, reduced with hydrogen and 10% palladium on charcoal catalyst and the solution filtered and neutralised to give 6-amino-7-hydroxy-1(2H)-phthalazinone.

(2) Treatment of 6-amino-7-hydroxy-1(2H)phthalazinone with methyl phosphate and subsequent treatment with boiling aqueous sodium hydroxide, and purification gives 6-dimethylamino-7-hydroxy-1(2H)-phthalazinone which may be converted into the sesquisulphate of the title compound by the general procedure of Example 1(iii–viii).

EXAMPLE 12

Substitution of isopropylamine and 2-phenylethylamine for t-butylamine in the general procedure of Example 1(iv–viii) leads to the production of the sulphates of 5-(3-isopropylamino-2-hydroxypropoxy)-1-hydrazinophthalazine and 5-(3-(2-phenylethylamino)-2-hydroxypropoxy)-1-hydrazinophthalazine, respectively

EXAMPLE 13

| Ingredients | Amounts |
| --- | --- |
| 5-(3-t-Butylamino-2-hydroxypropoxy)-1-hydrazinophthalazine sulphate | 100 mg |
| Sucrose | 40 mg |
| Starch | 15 mg |
| Talc | 3 mg |
| Stearic Acid | 1 mg |

The ingredients are screened, mixed and filled into a hard gelatin capsule.

EXAMPLE 14

| Ingredients | Amounts |
| --- | --- |
| 5-(3-t-Butylamino-2-hydroxypropoxy)-1-hydrazinophthalazine sulphate | 120 mg |
| Lactose | 60 mg |

The ingredients are screened, mixed and filled into a hard gelatin capsule.

Similarly, the other compounds of Formula 1 may be formulated into pharmaceutical compositions by the procedures of Examples 13 and 14.

The pharmaceutical compositions prepared as in the foregoing examples are administered to a subject within the dose ranges given above to block β-adrenergic receptors and cause vasodilatation.

We claim:

1. A compound of the formula:

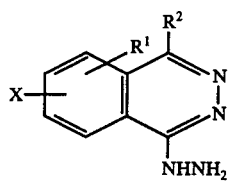

wherein $R^1$ is hydrogen, lower alkyl, halogen, lower alkoxy or di lower alkylamino; $R^2$ is hydrogen, methyl, halogen, benzyl, chlorobenzyl or methoxybenzyl; and X is a group of the formula

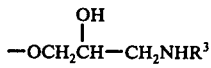

wherein $R^3$ is isopropyl, t-butyl or phenylethyl; or a pharmaceutically acceptable acid addition salt thereof.

2. A compound of claim 1 wherein $R^1$ is hydrogen, chloro or methyl.

3. A compound of claim 1 wherein $R^2$ is hydrogen or methyl

4. A compound of claim 1 wherein $R^3$ is isopropyl or t-butyl.

5. A compound of claim 1 wherein X is in the 5-position of the 1-hydrazinophthalazine ring.

6. A compound of claim 5 wherein $R^1$ is lower alkyl, halogen, lower alkoxy or di lower alkylamino and is in the 7- or 8-position of the 1-hydrazinophthalazine ring.

7. A compound of claim 1, said compound being 5-(3-t-butylamino-2-hydroxypropoxy)-1-hydrazinophthalazine.

8. A pharmaceutical composition having β-adrenergic blocking and vasodilator activity comprising in an effective amount to produce β-adrenergic blocking and vasodilator activity a compound of claim 1 in combination with a pharmaceutically acceptable diluent or carrier.

9. A method of concomitantly blocking β-adrenergic receptors and producing vasodilatation which comprises administering to an animal in need thereof in an effective amount to block said receptors and produce vasodilatation a compound of claim 1.

10. A method of treating angina pectoris which comprises administering to an animal in need thereof in an effective amount to treat angina pectoris a compound of claim 1.

11. A method of treating cardiac arrhythmia which comprises administering to an animal in need thereof in an effective amount to treat cardiac arrhythmia a compound of claim 1.

12. A method of treating hypertension which comprises administering to an animal in need thereof in an effective amount to treat hypertension a compound of claim 1.

* * * * *

UNITED STATES PATENT AND TRADEMARK OFFICE
CERTIFICATE OF CORRECTION

PATENT NO. : 4,093,725

DATED : June 6, 1978

INVENTOR(S) : Anthony Maitland Roe, Robert Antony Slater and Edwin Michael Taylor It is certified that error appears in the above—identified patent and that said Letters Patent are hereby corrected as shown below:

On the first page of the patent, in the left-hand column, in item [75], the name of the inventor reading "Robert Anthony Slater" should read -- Robert Antony Slater -- .

Column 1, Formula 2, that portion of the structural formula reading 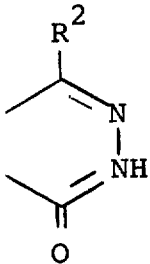 should read 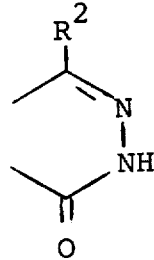

Column 4, Formula 7, that portion of the structural formula reading 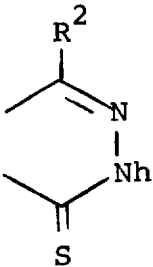 should read 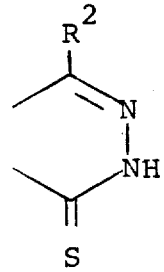

UNITED STATES PATENT AND TRADEMARK OFFICE
CERTIFICATE OF CORRECTION

PATENT NO. : 4,093,725

DATED : June 6, 1978

INVENTOR(S) : Anthony Maitland Roe, Robert Antony Slater and Edwin Michael Taylor It is certified that error appears in the above-identified patent and that said Letters Patent are hereby corrected as shown below:

Column 10, line 36, "Dimethylation" should read -- Demethylation --.

Signed and Sealed this

Fifteenth Day of May 1979

[SEAL]

Attest:

RUTH C. MASON
*Attesting Officer*

DONALD W. BANNER
*Commissioner of Patents and Trademarks*